United States Patent [19]

Gorman et al.

[11] Patent Number: 5,405,745
[45] Date of Patent: Apr. 11, 1995

[54] METHODS FOR DETECTING CANDIDA ALBICANS

[75] Inventors: Jessica A. Gorman, Yardley; Catherine A. Bingham, Newtown, both of Pa.

[73] Assignee: E. R. Squibb & Sons, Inc., Princeton, N.J.

[21] Appl. No.: 808,455

[22] Filed: Dec. 17, 1991

[51] Int. Cl.⁶ .................. C12Q 1/68; C12N 1/00
[52] U.S. Cl. ...................... 435/6; 435/921; 435/922
[58] Field of Search .......... 435/6, 922; 935/77, 935/78

[56] References Cited

PUBLICATIONS

J. Bacteriology 173(2): 842–850 (Jan. 1991).
Sadhu, C.; et al. "Telomeric and dispersed repeat . . . "
J. Bacteriology 164(1): 7–13 (1985).
Wills, Jr. "Circular Mitochondirial Gernome . . . "
Proc. Natl. Acad. Sci 85:1452–1456 (Mar. 1988).
Scherer, S; "A Candida albicans dispersed, . . . ".
Scherer, S. and D. A. Stevens, Proc. Natl. Acad. Sci USA 85, 1452–1456 (1988) "A Candida albicans dispersed, repeated gene family and its epidemiologic applications."
Schmid, J. et al.,J. Clin. Microbiol. 28, 1236–1243 (1990) "Computer-assisted methods for assessing strain relatedness in Candida albicans by fingerprinting with the moderately repetitive squence Ca3."
Sadhu, C. et al., J. Bacteriol. 173, 842–850 (1991) "Telomeric and dispersed repeat sequences in Candida yeasts and their use in strain identification."
Mason, M. M., et al., J. Clin. Microbiol. 25, 563–566 (1987) "Molecular probe for identification of medically important Candida species and Torulopsis glabrata."
Cutler, J. E., et al., J. Clin. Microbiol. 26, 1720–1724 (1988) "Candida albicansand Candida stellatoidea-specific DNA fragment."
Fox, B. C. et al.,J. Infectious Diseases 159, 488–494 (1989) "The use of a DNA probe for epidemiological studies of Candidiasis in immunocompromised hosts."
Magee, B. B., et al.,J. Bacteriol. 169, 1639–1643 (1987) "Strain and species identification by restriction fragment length polymorphisms in the ribosomal DNA repeat of Candida species."
Lasker, B. A., et al., Gene 102, 45–50 (1991) "Characterization of CARE-1: Candida albicans repetitive element-1."

Primary Examiner—Margaret Parr
Assistant Examiner—Eggerton Campbell
Attorney, Agent, or Firm—Timothy J. Gaul

[57] ABSTRACT

Isolated nucleic acid molecules capable of hybridizing to sequences of Candida albicans along with methods utilizing such probes for the detection of Candida albicans in clinical and other biological samples.

15 Claims, 3 Drawing Sheets

```
  1 TCGAAGCAAAAGTCTAAGAGATTAAAATTGTACCCTCAGTGAACGGAAGCTAAGTTATTG 60
 61 GGATTGGAAGTAGCAAGGGAATTGGGAAGTACTGAGAGAATGGACAGCCAAGTTATTGGA 120
121 AGTGGGAGTTGGATTTGGGAAAGAAAATCAGAGAATGAAAAATCACGCAAACTATTTTGA 180
181 AAAAACCCTGGCCAAGTTAATCAAGAGACAATAGCAATGGAGA 223
```

FIG. 1

```
   1 TACGTATCTCCAGAGGCCATAGAATGCACTCCTTTATTAGTACATTTCCTTATTAAACTA 60
  61 CACTATAGTATAGAATTGAAATACATTAATTTATATTATTATCACTACTCAAAGATAAGA 120
 121 TTCCTAAAGGTACTTTAACTTCTGAATAGTATGAAACTAAACGGTACCAATTAAACAGTC 180
 181 TGGCATGTTTTTACTCAAAAATTTTGATAAAATTAAGCAAAAAATTTTTTCTAAGTGCGG 240
 241 AGGGTTATGTAGTTGCTAAAAAGGGTTATACCTGACTATAAATACCAATCAATGAGAGCA 300
 301 AGGATGAGTTTGGTGTTTTCTTAAAGGGTTGATATCTTGTGAGTCAACAGTAAATCTTTT 360
 361 GTGTGATAGATTGCCCTTATAACAAGGAATATGTGTAGTTGTAGGTCAAGCAGTGTGAAT 420
 421 GTTGTAGTATAGAAAGGATCCACTAGAAGTATGGCTGTTTTGGTTGGGCTCACCAAGAAG 480
 481 TCTGATTTAGTACTGCAAAGTTTTTGCCAAAATGAGAAAAGTTGTACCGTCTCACCAAAA 540
 541 AATTGGATGGAATAAAAACTTTCAAAAACAGTTCACTTTCCACCACAGATGTATCCAACA 600
 601 CATTGACGTTGTTTGTGAACAAGTAGTCATTGGAATCCATACTAATGGAAACGCGAAAAA 660
 661 AAGATGGCAAAAATTTTTTTGCTAACAAATTTTGTTAGGCGCGAAAAAAAAGATGGCAAA 720
 721 GATTTTACAAGCTGTCAAAAAAAGATGACAAAAATTTACCAAGTTTTTTTGCGGTTTTTT 780
 781 TTATGGGTTTTTAGGGCTTGTATAGGTTGTTTAGGGGTGTAGGAATAGGATGGGCTGTGT 840
 841 TTGAGAGCGAACGGAGCACTGGTTGCCGAGATATGCGCGGTTAAAGGTGGGTGAGTGGAA 900
 901 AAGGCGGAAAAACAGTAGGTAGATGCCCACTTTTTGCACTTTTTAAAGCATCAGTAGATA 960
 961 GCTCTCACTCTGTAGATTCTACCTATCAAGGTTAGAAGTTGATACCTCTTTTGGTTGTTG 1020
1021 AGCTAGAGCCCGTTTTAGTCAGTTTTGGCCGATTTTACGACATTTTTTTGCCATCTTTTT 1080
1081 TTTAACTATGCGACTTTTTTTTGGTAGTGCGACATATTTTTGCCATCTTTTTTCTGCTCGC 1140
1141 GGGTTTAAGACCGCATTGCTAACAAATTTTGTTAGCAAGACCGCATGCGAAAATCAAGAC 1200
1201 CGCCGCAATAAAGACGTTTATAAACTATATAACATATAAATATAAACAATCCAAAGAAAA 1260
1261 AAATACAAAGTAAAAAAGTTCAAGGAGAAGGCATCCTAAAAGAAGGATACTATAAACTCC 1320
1321 TCATCAAGTAAATAAAATGTAAAGCAAACAATAGCAAATTCTTAATAGTAATAGGTTAAG 1380
1381 CAGTTAGAAACGGTGAGTGTGGTAGTAGTGGTATTTGAAGCCTCGAACCCATATTACAAA 1440
1441 GGAAGACTCATCTAGAGTGTTCCGATGGTGACCGTATCGCCAATGAATTTCAAGGGCGGT 1500
1501 GATCGCAGCAATGAAGCAGGACAAGGCAAGGTATTGTTTAGTAGTAAGTAGGGGGTTGGC 1560
1561 AATGTATGAGCTGAAGTGGTTCGATAAGTTGCGTGGTCCAAGTCGTTGCCAGGTTTTCTT 1620
1621 GGCCCATATGCATTGGCAGAATCGATGCTCGAGTGGAGTTGTAGTATATGGTTGCTCGCA 1680
1681 GAGGTCACAGTTTGGTTGTGAAAGTTTGTAGATGTGTGAGTGGCCCAAATTGAACCGATG 1740
1741 ATAGTGA 1747
```

FIG. 2

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 223 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:1:

| | | | | | |
|---|---|---|---|---|---|
| TCGAAGCAAA | AGTCTAAGAG | ATTAAAATTG | TACCCTCAGT | GAACGGAAGC | TAAGTTATTG | 60
| GGATTGGAAG | TAGCAAGGGA | ATTGGGAAGT | ACTGAGAGAA | TGGACAGCCA | AGTTATTGGA | 120
| AGTGGGAGTT | GGATTTGGGA | AAGAAAATCA | GAGAATGAAA | AATCACGCAA | ACTATTTTGA | 180
| AAAAACCCTG | GCCAAGTTAA | TCAAGAGACA | ATAGCAATGG | AGA | | 223

(2) INFORMATION FOR SEQ ID NO:2:

(i) SEQUENCE CHARACTERISTICS:
        (A) LENGTH: 1747 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

| | | | | | |
|---|---|---|---|---|---|
| TACGTATCTC | CAGAGGCCAT | AGAATGCACT | CCTTTATTAG | TACATTTCCT | TATTAAACTA | 60
| CACTATAGTA | TAGAATTGAA | ATACATTAAT | TTATATTATT | ATCACTACTC | AAAGATAAGA | 120
| TTCCTAAAGG | TACTTTAACT | TCTGAATAGT | ATGAAACTAA | ACGGTACCAA | TTAAACAGTC | 180
| TGGCATGTTT | TTACTCAAAA | ATTTTGATAA | AATTAAGCAA | AAAATTTTTT | CTAAGTGCGG | 240
| AGGGTTATGT | AGTTGCTAAA | AAGGGTTATA | CCTGACTATA | AATACCAATC | AATGAGAGCA | 300
| AGGATGAGTT | TGGTGTTTTC | TTAAAGGGTT | GATATCTTGT | GAGTCAACAG | TAAATCTTTT | 360
| GTGTGATAGA | TTGCCCTTAT | AACAAGGAAT | ATGTGTAGTT | GTAGGTCAAG | CAGTGTGAAT | 420
| GTTGTAGTAT | AGAAAGGATC | CACTAGAAGT | ATGGCTGTTT | TGGTTGGGCT | CACCAAGAAG | 480
| TCTGATTTAG | TACTGCAAAG | TTTTTGCCAA | AATGAGAAAA | GTTGTACCGT | CTCACCAAAA | 540
| AATTGGATGG | AATAAAAACT | TTCAAAAACA | GTTCACTTTC | CACCACAGAT | GTATCCAACA | 600
| CATTGACGTT | GTTTGTGAAC | AAGTAGTCAT | TGGAATCCAT | ACTAATGGAA | ACGCGAAAAA | 660
| AAGATGGCAA | AAATTTTTTT | GCTAACAAAT | TTTGTTAGGC | GCGAAAAAAA | AGATGGCAAA | 720
| GATTTTACAA | GCTGTCAAAA | AAAGATGACA | AAAATTTACC | AAGTTTTTTT | GCGGTTTTTT | 780
| TTATGGGTTT | TTAGGGCTTG | TATAGGTTGT | TTAGGGGTGT | AGGAATAGGA | TGGGCTGTGT | 840
| TTGAGAGCGA | ACGGAGCACT | GGTTGCCGAG | ATATGCGCGG | TTAAAGGTGG | GTGAGTGGAA | 900
| AAGGCGGAAA | AACAGTAGGT | AGATGCCCAC | TTTTTGCACT | TTTTAAAGCA | TCAGTAGATA | 960
| GCTCTCACTC | TGTAGATTCT | ACCTATCAAG | GTTAGAAGTT | GATACCTCTT | TTGGTTGTTG | 1020
| AGCTAGAGCC | CGTTTAGTC | AGTTTGGCC | GATTTACGA | CATTTTTTG | CCATCTTTTT | 1080
| TTTAACTATG | CGACTTTTTT | TTGGTAGTGC | GACATATTTT | TGCCATCTTT | TTCTGCTCGC | 1140
| GGGTTTAAGA | CCGCATTGCT | AACAAATTTT | GTTAGCAAGA | CCGCATGCGA | AAATCAAGAC | 1200
| CGCCGCAATA | AAGACGTTTA | TAAACTATAT | AACATATAAA | TATAAACAAT | CCAAAGAAAA | 1260
| AAATACAAAG | TAAAAAGTT | CAAGGAGAAG | GCATCCTAAA | AGAAGGATAC | TATAAACTCC | 1320
| TCATCAAGTA | AATAAAATGT | AAAGCAAACA | ATAGCAAATT | CTTAATAGTA | ATAGGTTAAG | 1380
| CAGTTAGAAA | CGGTGAGTGT | GGTAGTAGTG | GTATTTGAAG | CCTCGAACCC | ATATTACAAA | 1440
| GGAAGACTCA | TCTAGAGTGT | TCCGATGGTG | ACCGTATCGC | CAATGAATTT | CAAGGGCGGT | 1500
| GATCGCAGCA | ATGAAGCAGG | ACAAGGCAAG | GTATTGTTTA | GTAGTAAGTA | GGGGGTTGGC | 1560
| AATGTATGAG | CTGAAGTGGT | TCGATAAGTT | GCGTGGTCCA | AGTCGTTGCC | AGGTTTTCTT | 1620
| GGCCCATATG | CATTGGCAGA | ATCGATGCTC | GAGTGGAGTT | GTAGTATATG | GTTGCTCGCA | 1680
| GAGGTCACAG | TTTGGTTGTG | AAAGTTTGTA | GTATGTGTAG | TGGCCCAAAT | TGAACCGATG | 1740
| ATAGTGA | | | | | | 1747

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GTAGTACTGG TACCCGTCCT GTGGATC        27

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GTAAGCTTCC CACCCGGGAT C        21

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

TTGCTAACAA ATTTTGTTAG        20

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

AAAAAAGAT GGCAAAATT TTTC        24

METHODS FOR DETECTING CANDIDA ALBICANS

BACKGROUND OF THE INVENTION

The organism *Candida albicans* is a yeastlike imperfect fungus of the family Cryptococcaceae, order Moniliales, characterized by producing yeast cell, mycelia, pseudomycelia and blastospores. This organism is commonly part of the normal flora of the skin, mouth, intestinal tract and vagina, but under certain conditions can cause a variety of infections, including vaginitis, thrush, dermatocandidiasis and bronchocandidiasis. Such infections are particularly problematic in immunocompromised individuals, such as those with AIDS.

Although methods have been developed for the detection of fungal infections, these methods often fail to discriminate between *Candida albicans* and other Candida species. Thus, the need exists for improved methods for the detection of *Candida albicans*.

SUMMARY OF THE INVENTION

The present invention concerns an isolated deoxyribonucleic acid (DNA) molecule comprising a DNA sequence having all or part of the nucleotide sequence as shown in SEQ. ID. NO.: 1 or SEQ. ID. NO.: 2, or a DNA sequence complementary to one of these DNA sequences.

The present invention also concerns methods for detecting *Candida albicans* DNA sequences.

DESCRIPTION OF THE DRAWINGS

FIG. 1. A 223 bp Sau3A restriction enzyme fragment that contains the repetitive DNA Rel1 was sequenced using the dideoxy chain-termination method [Sanger, F., et al., *Proc. Natl. Acad. Sci.* USA 74, 5463–5467 (1977)] (See SEQ. ID. NO.: 1). The A-rich strand is shown.

FIG. 2. The sequence of the repetitive DNA Rel2. A 2.8 kb DNA fragment containing a repetitive DNA element was cloned. Subcloning and hybridizations indicated that the repetitive sequence was contained in a 1747 bp fragment delineated by a SnaBI restriction site and the vector cloning site. The DNA sequence of this fragment is presented (See SEQ. ID. NO.: 2).

DETAILED DESCRIPTION OF THE INVENTION

Figures 3A, 3B:
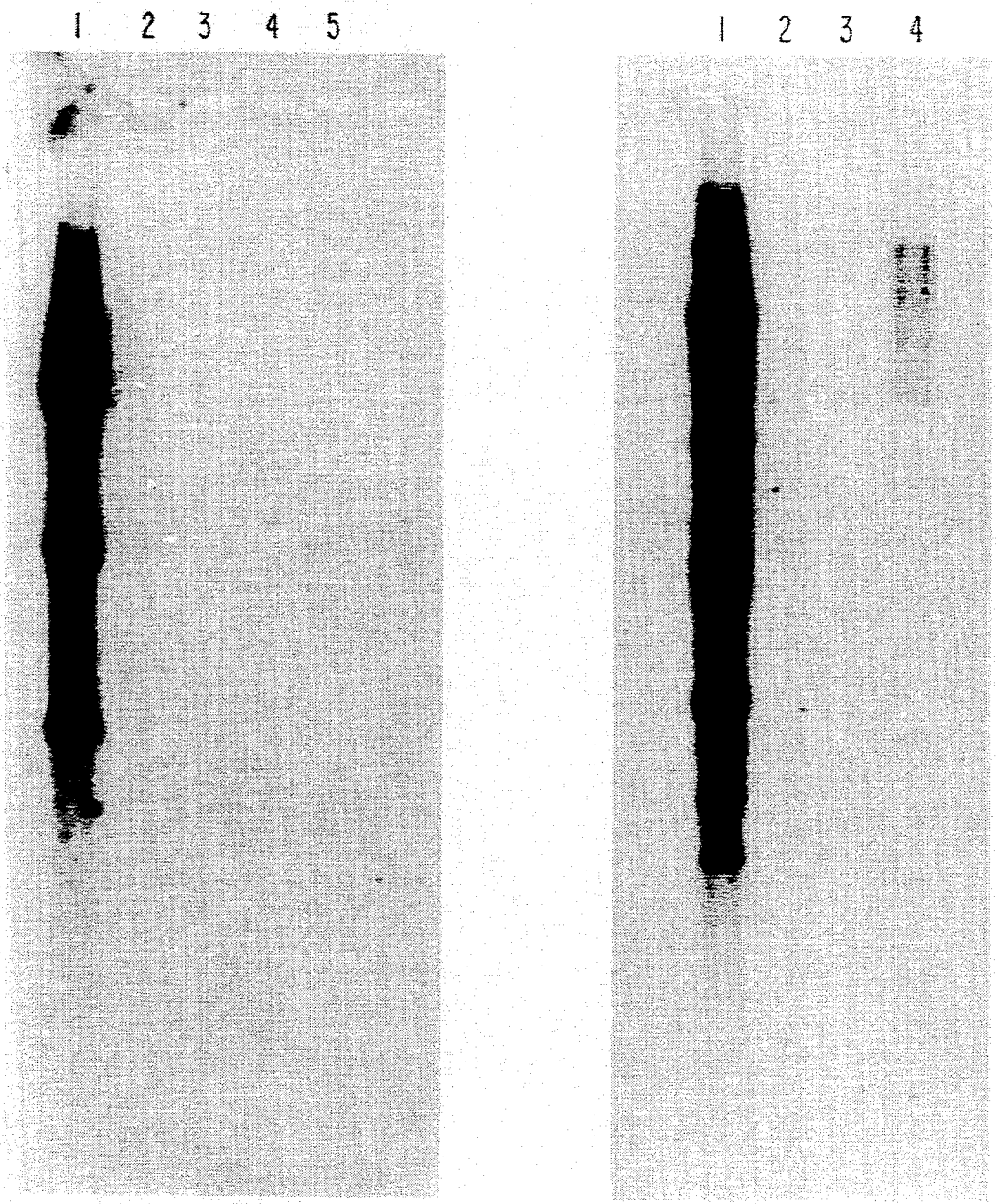
FIG. 3. Hybridization of Rel1 and Rel2 to Candida species. Total genomic DNA was isolated from *Candida albicans* and 4 other species of Candida. The DNA was digested with EcoRI and was electrophoresed on a 1% agarose gel. The gel was dried and hybridized with Rel1 (A) or Rel2 (B). Lane 1, *Candida albicans*; lane 2, *Candida krusei*; lane 3, *Candida tropicalis*; lane 4, *Candida stellatoidea*; lane 5, *Candida utilis*.

The present invention is based in part on the discovery by Applicants of certain DNA sequences in the genome of *Candida albicans* which are not present at detectable levels in the genome of other Candida species. The detection of these DNA sequences in a sample is indicative of the presence of *Candida albicans* in the sample, and is particularly useful for distinguishing *Candida albicans* from other Candida and yeast species.

Thus, the present invention concerns a method for detecting the presence of a *Candida albicans* DNA sequence in a sample comprising contacting the sample with a detectable marker which comprises a nucleic acid probe that is based on the nucleic acid sequence as shown in SEQ. ID. NO.: 1 or SEQ. ID. NO.: 2, preferably the nucleic acid sequence as shown in SEQ. ID. NO.: 5, SEQ. ID. NO.: 6 or corresponding to nucleotides 656–1175 as shown in SEQ. ID. NO.: 2, and determining whether the sample binds the detectable marker. The presence of bound detectable marker indicates the presence of *Candida albicans* DNA in the sample.

The nucleic acid sequence to be detected is a DNA sequence having all or part of the nucleotide sequence as shown in SEQ. ID. NO.: 1 or SEQ. ID. NO.: 2, preferably having the nucleotide sequence as shown in SEQ. ID. NO.: 5, SEQ. ID. NO.: 6, or of nucleotides 656–1175 as shown in SEQ. ID. NO.: 2, or a DNA sequence complementary to one of these DNA sequences. A DNA sample containing the DNA sequence to be detected can be isolated using various methods for DNA isolation which are well-known to those of ordinary skill in the art. The organism for identification is first isolated from a clinical specimen. Many types of specimens from patients can be utilized, for example, blood, faeces, sputum, urine or vaginal swab. The general procedures for specimen isolation are well known in the art, and are described by F.C. Odds (in Candida and Candidosis, A Review and Bibliography; 2nd edition, (1988) Bailliere Tindall).

A genomic DNA sample can then be isolated from the organism by subjecting intact cells to mechanical breakage, for example, by vortexing cells in the presence of glass beads. Cells can also be lysed enzymatically in hypotonic buffer. Once cells are lysed, cell debris can be removed by centrifugation. The bulk of cellular protein can be removed by phenol extraction and RNA (ribonucleic acid) can be degraded by the addition of RNase. The genomic DNA can then be precipitated, for example, with ethanol in the presence of sodium acetate.

The detectable marker useful for detecting a DNA sequence having all or part of the nucleotide sequence as shown in SEQ. ID. NO.: 1 or SEQ. ID. NO.: 2, or a DNA sequence complementary to one of these DNA sequences, can be a labeled nucleic acid (DNA or RNA) sequence having a nucleotide sequence complementary to at least a portion of the DNA sequence to be detected, and can be as small as 15 nucleotides in length, although lengths greater than about 200 nucleotides are preferred.

The detectable markers of the present invention can be labeled with commonly employed radioactive labels, such as $^{32}$P and $^{35}$S, to allow their detection. Other labels such as biotin or mercury can also be employed. Various methods well-known to those of ordinary skill in the art can be used to label the detectable markers. For example, DNA sequences and RNA sequences can be labeled with $^{32}$P or $^{35}$S using the random primer method as described in Feinberg, A. D. and Vogelstein, B., Anal. Biochem. 132, 6–13 (1983).

Once a suitable detectable marker has been obtained, various methods well-known to those of ordinary skill in the art can be employed for contacting the detectable marker with the sample of interest. For example, DNA-DNA and DNA-RNA hybridizations can be performed using standard procedures known in the art. In a typical DNA-DNA hybridization procedure for detecting the DNA sequences to be detected in genomic DNA, the genomic DNA is first isolated as discussed herein above, and then bound to a solid support membrane such as a nitrocellulose or nylon membrane. The DNA on the membrane is then denatured and a radiolabeled nucleic acid probe is hybridized to the immobilized genomic DNA. The filter is then washed to remove unbound or weakly bound probe, and is then autoradiographed to determine if the genomic DNA sample contains sequences that have hybridized with the probe.

The presence of bound detectable marker can be detected using various methods well-known to those of ordinary skill in the art. For example, if the detectable marker is radioactively labeled, autoradiography can be employed. Depending on the label employed, detection by spectrophotometric, enzymatic or immunological methods can also be used.

The present invention also concerns an isolated DNA molecule comprising a DNA sequence having all or part of the nucleotide sequence as shown in SEQ. ID. NO.: 1 or SEQ. ID. NO.: 2, preferably having the nucleotide sequence as shown in SEQ. ID. NO.: 5, SEQ. ID. NO.: 6, or of nucleotides 656–1175 as shown in SEQ. ID. NO.: 2, or a DNA sequence complementary to one of these DNA sequences.

The DNA sequences of the present invention can be obtained using various methods well-known to those of ordinary skill in the art. At least three alternative principal methods can be employed:

(1) the isolation of a double-stranded DNA sequence from genomic DNA which contains the sequence;
(2) the chemical synthesis of the DNA sequence; and
(3) the synthesis of the DNA sequence by polymerase chain reaction (PCR).

In the first approach, a genomic DNA library can be screened in order to identify a DNA sequence having all or part of the nucleotide sequence as shown in SEQ. ID. NO.: 1 or SEQ. ID. NO.: 2, or a DNA sequence complementary to one of these DNA sequences. For example, a *Candida albicans* genomic DNA library can be screened in order to identify these DNA sequences. Various *Candida albicans* genomic DNA libraries, for example, pYSK35 [Fling, M. E. et al., *Mol. Gen. Genet.* 227, 318–329 (1991)], pCARS1 [Kelly, R. et al., *Mol. Gen. Genet.* 214, 24–31 (1988)] and YEp13 [Gillum, A.M. et al., *Mol. Gen. Genet.* 198, 179–182 (1984)], can be employed. Various techniques can be used to screen the genomic DNA library.

For example, labeled single stranded DNA probe sequences duplicating a sequence present in the target genomic DNA sequence can be employed in DNA/DNA hybridization procedures carried out on cloned copies of the genomic DNA which have been denatured to single stranded form.

In one typical screening method suitable for hybridization techniques, the genomic DNA library, which is often contained in a yeast shuttle vector, such as YEp13, is transformed into *E. coli*. *E. coli* transformants are then plated on agar plates and then transfered onto filter membranes, for example, nitrocellulose membranes. The *E. coli* cells are then lysed on the membranes and a DNA probe can then be hybridized to the filters to identify those tranformants containing the genomic DNA sequence having all or part of the nucleotide sequence as shown in SEQ.ID.NO.: 1 or SEQ.ID.NO.:2.

In the second approach, the DNA sequences of the present invention can be chemically synthesized. For example, DNA sequences having all or part of the nucleotide sequence as shown in SEQ.ID. NO.: 1 or SEQ. ID. NO.: 2, or DNA sequence complementary to these DNA sequences, can be synthesized as a series of 100 base oligonucleotides that can then be sequentially ligated (via appropriate terminal restriction sites) so as to form the correct linear sequence of nucleotides.

In the third approach, the DNA sequences of the present invention can be synthesized using polymerase chain reaction (PCR). Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

The DNA sequences of the present invention can be used in a variety of ways in accordance with the present invention. For example, they can be used as DNA probes as described herein above.

The nucleotide sequences of the DNA sequences of the present invention may be determined by various methods known in the art. For example, the dideoxy chain termination method as described in Sanger et al., *Proc. Natl. Acad. Sci.* USA 74, 5463–5467 (1977), or the Maxam-Gilbert method as described in *Proc. Natl. Acad. Sci.* USA 74, 560–564 (1977) may be employed.

The following example is further illustrative of the present invention. This example is not intended to limit the scope of the present invention, and provides further understanding of the invention.

EXAMPLE

I. Materials and Methods

A. Strains used in this study

*Candida albicans* strain B-792P1 obtained from J. Kwon-Chung (National Institutes of Health, Bethesda, Md.) was used in the screen to identify the repeats. *Candida albicans* strains A-81Pu and B-792P1 [Kwon-Chung, K. J. and Hill, W. B., Sabouradia 8, 48–59 (1970)], FC18 [Whelan, W. L. et al., *Mol. Gen. Genet.* 180, 107–113 (1980)] and 1006 [Goshorn, A. K. and Scherer, S., Genetics 123, 667–673 (1989)] obtained from S. Scherer (University of Minnesota, Minneapolis, Minn.), were used for further characterization of the repeats. *Candida krusei* SC2968, *Candida utilis* SC14001 (ATCC 22023), *Candida tropicalis* SC8159 (ATCC 13803), *Candida stellatoidia* SC11342 (ATCC 36232), *Candida guillermondi* SC2997, *Candida parakrusei* SC5316, *Candida pseudotropicalis* SC11241, *Candida parapsislosis* SC14988 (ATCC 22019), *Schizosaccharomyces pombe* SC12886, and *Saccharomyces cerevisiae* 108-11b (provided by C. Bingham) were used to determine the distribution of the repeats among other yeast and Candida species. All strains are on deposit in the Bristol-Myers Squibb Culture Collection, Wallingford, Conn.

B. Preparation of plasmid DNA pools

Competent *E. coli* cells (strain HB101, GIBCO BRL) were transformed with the *Candida albicans* pYSK35 genomic library [Fling, M. E. et al., *Mol. Gen. Genet.* 227, 318–329 (1991)]. *E. coli* transformation was performed as described by Maniatis, T. et al., Molecular Cloning: a laboratory manual, Cold Spring Harbor Laboratory, Cold Spring Harbor, N.Y. (1982). Two thousand individual transformants were streaked on agar plates. Transformants were pooled into 200 groups of 10 and plasmid DNA was prepared from each pool using the alkaline lysis minipreparation procedure as described in Maniatis, T. et al., supra. Approximately 400 ng of each miniprep DNA was digested with the restriction enzyme XbaI to linearize the plasmids.

C. Rotating-gel electrophoresis

Chromosome length DNA was prepared from strain B-792P1 by embedding cells in agarose microbeads as described in Carle, B. F. and Olson, M. V., Methods in Enzymology 155, 408–482 (1987) with the following modifications. Microbeads prepared with Seakem GTG (FMC Bioproducts, Rockland, Me.) agarose were preincubated in spheroplasting buffer for 30 minutes prior to the additon of Zymolyase 100T (Seikagaku Kogyo Co., Ltd., Tokyo, Japan). After Zymolyase was added, beads were incubated at 37° C. and were monitored periodically by adding an aliquot of microbeads to lysis buffer on a microscope slide. When greater than 70% of the cells were lysed the beads were pelleted and then resuspended in 5 ml of lysis buffer at 50° C. as described. Electrophoresis was performed using a Rotating-gel electrophoretic apparatus as described in Smith, S. et al., Science 243, 203–206 (1989). Sample beads (30 μl) were loaded into wells and the wells were sealed with agarose.

Gels were run at 5 V/cm, 2 minutes pulse time, 8° C. for 20.5 hours in 0.5 × TBE buffer (Maniatis et al., supra), using a 120° C. rotation angle (60°± from the origin). Rotating gels were denatured using standard techniques as described in Maniatis, T. et al., supra. Gels were then dried as described in Tsau, S. G. S. et al., Anal. Biochem 131, 365–32 (1983), and individual lanes were used for hybridization.

D. Genomic DNA analysis

Total genomic DNA from each Candida strain was prepared using a glass bead cell lysis procedure. [See, Hoffman, C. S. and Winston, F., Gene 57, 267–272 (1987)]. Briefly, 1.5 ml of a stationary phase culture was pelleted and the cells were resuspended in lysis buffer. Glass beads were then added and the suspension was vortexed 4 times, 2 minutes each with 30 second intervals between pulses. The suspension was pelleted and the supernatent was collected. RNase was added to the supernatent and the DNA was then precipitated with ethanol.

DNA, 1 μg, was digested to completion with the indicated restriction enzymes. Digested DNA was electrophoresed in 1.0% Seakem LE agarose for 480 volt hours in 1 × TBE buffer. Gels were denatured and dried as described above for the rotating gels.

E. DNA Hybridization

Linearized DNA (100 ng) was labeled with $\alpha$-$^{32}$P dCTP by random primer extension as described in Feinberg, A. P. and Vogelstein, B., Anal. Biochem. 132, 6–13 (1983). Dried gels were hybridized in a maximum of 10 ml of hybridization solution (7% SDS, 0.3M NaPO4, pH 7.2, and 1 mM EDTA). Labeled probe ($2\times10^5$ cpm/ml of hybridization solution) was added to the gel and the gel was then placed in a 65° C. gyrotory water bath for 12 to 18 hours. Gels were washed 2×5 minutes each, in 5% SDS, 0.3M NaPO4, pH7.2, 1 mM EDTA and then 7×5 minutes each in 1% SDS, 0.3M NaPO4, pH7.2, 1 mM EDTA. Gels were then wrapped in Saran Wrap to keep them damp and were autoradiographed at −80° C.

F. DNA Sequencing

DNA fragments containing the repeats were cloned into the plasmid vector pBSII SK+ (Stratagene, La Jolla, Calif.). DNA sequencing was essentially as described in Sanger, F., et al., Proc. Natl. Acad. Sci. USA 74, 5463–5467 (1977). Sequencing primers were obtained from Stratagene or were synthesized using a DNA synthesizer (Applied Biosystems, Foster City, Calif.). Sequencing reaction buffers were obtained from United States Biochemical, Cleveland, Ohio.

G. PCR

For DNA hybridization, a full length Rel1 repeat fragment containing minimal vector sequences was made by PCR using primers based on the vector DNA sequences adjacent to the cloning site in pYSK35. The sequences of the primers are GTAGTACTG-GTACCCGTCCTGTGGATC [SEQ. ID. NO.: 3] and GTAAGCTTCCCACCCGGGATC [SEQ. ID. NO.:4]. PCR was performed using standard procedures [See, Saiki, R. K. et al., Science 239, 487–491 (1988)].

H. Quantitative Hybridizations

Total genomic DNA from the indicated Candida albicans strains was diluted to 1 μg/ml in TE pH7.5. The DNA was then serially diluted 2-fold and 3-fold in water. Slots blots of the dilution series were made such that the most concentrated slot in the 1:2 dilution series contained a total of 1 μg of DNA and the most diluted slot contained a total of 7.8 ng of DNA for the 2-fold dilution. Similarly, the most concentrated slot in the 1:3 dilution series contained 1 μg of DNA and the most diluted slot contained 1.4 ng of DNA. Duplicate slots were probed with a 275 bp PCR fragment containing the Rel1 repeat and a 290 bp PCR fragment containing a portion of the Candida albicans TRP1 gene, the single copy control DNA. A second set of slots was probed with either a 1.75 kb HincII fragment containing the 1.4 kb Rel2 repeat, or a 2.8 kb EcoRI fragment containing the Candida albicans LEU2 gene, the single copy control DNA. Hybridizations were performed as described above. The intensities of the bands on the autoradiograms were quantitated by scanning the autoradiograms on an LKB scanning densitometer. The copy number of the repetitive DNAs was determined by comparing the quantitative data of the repeats and the single copy control DNAs.

II. RESULTS

A. Identification of the Repeat Sequences

A Candida albicans DNA library was screened for clones that hybridized to every Candida albicans chromosome as judged by hybridization to chromosomes separated on pulse-field gels. E. coli was transformed with a Candida albicans DNA library and transformants were pooled into groups of 10. Plasmid DNA was prepared from each pool and was then linearized with XbaI, labeled with $\alpha$-$^{32}$P dCTP and hybridized to strips of B-792P1 chromosomes on which 5 individual chromosome homologues were separated and the remaining chromosomes migrated as a large unresolved band. Pools that gave hybridization to all 6 bands (5 resolved chromosomes and the unresolved band) would be examined further. Ten of the first twenty pools screened contained clones that hybridized to 6 bands. Three of these pools were examined in more detail.

Plasmid DNA was prepared from the individual transformants in 3 of the 10 positive pools (30 individual transformants). Ten clones that hybridized to all 6 chromosome bands were identified. Nine of these appeared to contain the same small, 230–250 bp, insert. This insert was designated Rel1 (Repetitive element). The remaining clone contained a larger, 2.7 kb, insert that was designated Re12.

B. Characterization of the repeats

Re11 and Re12 are each present in at least 6 copies per cell in strain B-792P1, as determined by their hybridization to 6 bands on a pulse-field gel. The repeats were hybridized to additional pulse-field gels to see if they were present on every chromosome in B-792P1 and to examine their distribution in several other Candida albicans strains. Chromosome length DNAs of Candida albicans strains A-81Pu, B-792P1, FC18, B311, SC5314 and ATCC10261 were electrophoresed on pulse-field gels under three different conditions designed to resolve small, medium and large chromosomes. The gels were dried and then probed with either a PCR fragment containing the Re11 repeat or with a 2.7 kb HindIII-SmaI restriction fragment containing the Re12 repeat. Both Re11 and Re12 hybridize to most, if not all, of the resolvable chromosomes in the six Candida albicans strains examined. This data suggests that the copy number of the repeats is at least 8–16 copies per cell.

Quantitative DNA hybridizations were done, for three of these strains, A-81Pu, B-792P1 and FC18, as an independant measure of the copy number of the repeats. Total genomic DNA from each strain was serially diluted as described above, and was then aliquoted onto Nytran membranes using a slot-blot apparatus. Duplicate filters were probed with either the repetitive DNAs or with single copy control DNA. The resulting autoradiograms were scanned with a densitometer to quantitate the intensity of the hybridization signals. The data suggest that Re12 is present in approximately 14 copies per cell in strains A-81Pu and FC18 and 28 copies per cell in B-792P1 and that Re11 is present in approximately 32 copies per cell in each of these strains.

Re11 and Re12 are present in all the Candida albicans strains which have been examined (7 strains to date). To see if these repeats are present in other Candida and yeast species, DNA was prepared from 8 species of Candida and from Schizosaccharomyces pombe and Saccharomyces cerevisiae. The DNA was digested with EcoRI and gels were hybridized with Re11 and Re12. EcoRI digested Candida albicans DNA was included as a positive hybridization control. The results of the Re11 hybridization to 4 of the Candida species is shown in FIG. 3A. Even after prolonged exposure of the gel, no hybridization could be detected to the Candida Krusei, Candida tropicalis, Candida utilis or Candida stellatoida DNAs. Similar results were seen when hybridization to the other Candida and yeast species listed in the Materials and Methods were performed.

When the same experiment was done using Re12 DNA as a probe, no hybridization to any of the species was seen on exposures sufficient to visualize the Candida albicans hybridization signal. However, a very faint multi-band hybridization signal was observed with the Candida stellatoidia DNA after prolonged exposures (FIG. 3B). The relatively faint hybridization signal compared to that seen for Candida albicans strain B-792P1 suggests that Re12 is present in Candida stellatoidia but that the sequence of this repeat has diverged between the two species. The difference in hybridization intensity allows one to easily distinguish between Candida albicans and Candida stellatoidia DNAs.

The complete sequence of Re11 and Re12 have been determined. The Re11 sequence is presented in FIG. 1 [SEQ. ID NO.:1]. The Sau3A fragment that contains the repeat is A/T rich (61% A+T) and has an asymetric distribution of nucleotides. The A-rich strand shown in FIG. 1, has 89 A, 27 C 47 T and 60 G nucleotides.

The 2.8 kb fragment containing the Re12 repeat was sequenced. However, additional hybridizations (data not shown) indicated that part of this clone contained unique DNA. The sequence of the repetitive portion of the clone is shown in FIG. 2 [SEQ.ID NO.:2]. The sequence is 1747 nucleotides in length and is AT rich, (63% A+T).

Computer analysis of the Re12 sequence revealed the presence of two different subrepeat families in the region between bp 656 and bp 1175. Two copies of the sequence TTGCTAACAAA TTTTGTTAG [SEQ. ID. NO. 5] are present, one at bp 678 and one at bp 1156.

A second repeat with the consensus sequence AAAAAAAGATGGCAAAAATTTTTC [SEQ. ID. NO. 6] is present 5 times in the same region of Re12. Three tandem, directly repeated copies of near matches (21/24 bp) to the consensus sequence SEQ. ID. NO.: 6 lie between bp 656 and 760. Two more tandem indirect repeats are present between bp 1057 and 1135.

The presence of numerous copies of subrepeats in this 509 bp region of the Re12 sequence suggests that this might be the sequence of choice for hybridization probes.

The Re11 and Re12 sequences were compared using a DNA matrix analysis (IBI Pustell) and the results indicated that these two DNAs do not share common sequences. This finding is supported by hybridization data that showed Re11 did not cross-hybridize with Re12.

---

What is claimed is:

1. A method for detecting a *Candida albicans* DNA sequence in a sample comprising contacting the sample with a detectable marker which comprises a nucleic acid sequence having at least 15 sequential nucleotides from the DNA sequence shown in SEQ. ID. NO.: 1 or SEQ. ID. NO.: 2 and determining whether the sample binds the detectable marker, the presence of bound marker indicating the presence of *Candida albicans* in the sample.

2. The method according to claim 1 wherein the DNA sequence to be detected has all or at least 15 sequential nucleotides from the nucleotide sequence as shown in SEQ. ID. NO.: 1 or SEQ. ID. NO.: 2.

3. The method according to claim 2 wherein the DNA sequence to be detected has the nucleotide sequence as shown in SEQ. ID. NO.: 5, SEQ. ID. NO.: 6, or of nucleotides 656–1175 as shown in SEQ. ID. NO.: 2.

4. The method according to claim 1 wherein the DNA sequence to be detected is complementary to all or at least 15 sequential nucleotides from the nucleotide sequence as shown in SEQ. ID. NO.: 1 or SEQ. ID. NO.: 2.

5. The method according to claim 4 wherein the DNA sequence to be detected is complementary to the nucleotide sequence as shown in SEQ. ID. NO.: 5, SEQ. ID. NO.: 6, or to nucleotides 656–1175 as shown is SEQ. ID. NO.: 2.

6. The method according to claim 1 wherein the detectable marker comprises a DNA sequence having all or at least 15 sequential nucleotides from the nucleotide sequence as shown in SEQ. ID. NO.: 1 or SEQ. ID. NO.:2.

7. The method according to claim 6 wherein the DNA sequence has the nucleotide sequence as shown in SEQ. ID NO.: 5, SEQ. ID. NO. NO.: 6, or of nucleotides 656 to 1175 as shown in SEQ. ID. NO.: 2.

8. The method according to claim 1 wherein the detectable marker comprises a DNA sequence complementary to all or at least 15 sequential nucleotides from the nucleotide sequence as shown in SEQ. ID. NO.: 1 or SEQ. ID. NO.: 2.

9. The method according to claim 8 wherein the DNA sequence is complementary to the nucleotide sequence as shown in SEQ. ID. NO.: 5, SEQ. ID. NO.: 6, or to nucleotides 656–1175 as shown in SEQ. ID. NO.: 2.

10. The method according to claim 1 wherein the detectable marker comprises a RNA sequence having all or at least 15 sequential nucleotides from the nucleotide sequence as shown in SEQ. ID. NO.: 1 or SEQ. ID. NO.: 2.

11. The method according to claim 10 wherein the RNA sequence has the nucleotide sequence as shown in SEQ. ID. NO.: 5, SEQ. ID. NO.: 6, or to nucleotides 656–1175 as shown in SEQ. ID. NO.: 2.

12. The method according to claim 1 wherein the detectable marker comprises a RNA sequence complementary to all or at least 15 sequential nucleotides from the nucleotide sequence as shown in SEQ. ID. NO.: 1 or SEQ. ID. NO.: 2.

13. The method according to claim 12 wherein the RNA sequence is complementary to the nucleotide sequence as shown in SEQ. ID. NO.: 5, SEQ. ID. NO.: 6, or to nucleotides 656–1175 as shown in SEQ. ID. NO.: 2.

14. The method according to claim 1 wherein the detectable marker is labelled with a radioisotope.

15. The method according to claim 8 wherein the detecting is by autoradiography.

* * * * *